(12) United States Patent  
Lui et al.

(10) Patent No.: US 9,200,750 B2  
(45) Date of Patent: Dec. 1, 2015

(54) WALL STAND

(71) Applicant: GE Medical Systems Global Technology Company, LLC, Waukesha, WI (US)

(72) Inventors: Xiumin Lui, Beijing (CN); Bin Ye, Beijing (CN); Yannan Huang, Beijing (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 86 days.

(21) Appl. No.: 13/752,412

(22) Filed: Jan. 29, 2013

(65) Prior Publication Data

US 2013/0193295 A1 Aug. 1, 2013

(30) Foreign Application Priority Data

Jan. 30, 2012 (CN) .......................... 2012 1 0031588

(51) Int. Cl.
| H05G 1/02 | (2006.01) |
| F16M 13/02 | (2006.01) |
| A61B 6/10 | (2006.01) |
| A61B 6/00 | (2006.01) |
| G03B 42/02 | (2006.01) |
| A61B 6/04 | (2006.01) |

(52) U.S. Cl.
CPC .............. *F16M 13/022* (2013.01); *A61B 6/102* (2013.01); *A61B 6/4283* (2013.01); *A61B 6/4452* (2013.01); *G03B 42/025* (2013.01); *A61B 6/0407* (2013.01)

(58) Field of Classification Search
CPC ...... A61B 6/102; A61B 6/105; A61B 6/4464; A61B 6/4462; A61B 4/4476; A61B 6/4452; A61B 6/4283
USPC ........................... 248/415, 416; 378/193, 189
See application file for complete search history.

(56) References Cited

U.S. PATENT DOCUMENTS

| 6,851,851 B2 * | 2/2005 | Smith et al. ................... 378/189 |
| 7,441,952 B2 * | 10/2008 | Haupl et al. ................... 378/189 |
| 2006/0083353 A1 * | 4/2006 | Boomgaarden ............... 378/196 |
| 2006/0126795 A1 | 6/2006 | Lumma |

FOREIGN PATENT DOCUMENTS

| KR | 100920751 B1 | 10/2009 |
| KR | 101105624 B1 | 1/2012 |

OTHER PUBLICATIONS

European Search Report, Apr. 29, 2013, European Application No. 13151916.

* cited by examiner

*Primary Examiner* — Todd M Epps  
(74) *Attorney, Agent, or Firm* — GE Global Patent Operation; Marc A. Vivenzio

(57) ABSTRACT

A wall stand comprising a column, a detector box, a support arm configured to support the detector box, a rotary shaft mounted on the support arm, a rotary bracket attached to the detector box, wherein the rotary bracket is rotatable around the rotary shaft, and a drive mechanism configured to move the detector box on a plane supported by the rotary bracket in a direction perpendicular to an axial direction of the rotary shaft.

15 Claims, 6 Drawing Sheets

WALL STAND

BACKGROUND OF THE INVENTION

1. Field of the Invention

Embodiments of the present invention relate to medical imaging equipment and, in particular, a device for taking X-rays.

2. Description of the Prior Art

A wall stand is required when X-raying a patient. In case of radiographing an emergency patient, a wall stand further needs to operate in association with a stretcher table, and thus space between the column of the wall stand column and the detector box on the wall stand should suffice to ensure that the stretcher table can be placed in an appropriate position. In addition, doctors sometimes need to take a plurality of X-rays to mosaic a panoramic radiograph.

Currently there exist two kinds of wall stands.

The first kind of wall stand is shown in FIG. 1A. This kind of wall stand has a relatively short support arm 105, and therefore, the following problem arises: when used with a stretcher table 104, the top of a column 102 of the wall stand will collide with an overhead tube system 101. In other words, this kind of wall stand can only be used alone.

The other kind of wall stand is shown in FIG. 1B. In order to enable this kind of wall stand to operate in association with a stretcher table 104, it is necessary to design a fairly long support arm 105 to prevent the top of a column 102 of the wall stand from collision with an overhand tube system 101, which, however, gives rise to an overlarge footprint during installation and application of the wall stand.

The two kinds of existing wall stands are also subject to a common problem. When doctors need to take a plurality of X-rays for mosaicking a panoramic radiograph, since a detector box 103 on the wall stand is stationary, they have to move the stretcher table 104 by themselves, thus complicating their operation and causing patient discomfort, as shown in FIG. 2.

BRIEF SUMMARY OF THE INVENTION

According to an embodiment of the present invention, there is provided a wall stand. The wall stand comprises a column, a detector box, a support arm configured to support the detector box, a rotary shaft mounted on the support arm, a rotary bracket attached to the detector box, wherein the rotary bracket is rotatable around the rotary shaft, and a drive mechanism configured to move the detector box on a plane supported by the rotary bracket in a direction perpendicular to an axial direction of the rotary shaft.

BRIEF DESCRIPTION OF THE DRAWINGS

These and other advantages and features will be more understood from the following detailed description of preferred embodiments of the invention that is provided in connection with the accompanying drawings, wherein.

DETAILED DESCRIPTION OF EXEMPLARY EMBODIMENTS OF THE INVENTION

The present invention is further described below in terms of embodiments in connection with the drawings. Embodiments of the present invention relate to medical imaging equipment, according to an embodiment, there is provided a wall stand comprising a column, a detector box, a support arm for the detector box, a rotary shaft mounted on the support arm, a rotary bracket for the detector box capable of rotating around the rotary shaft, and a drive mechanism capable of moving the detector box in a plane supported by the rotary bracket in a direction perpendicular to an axial direction of the rotary shaft. The wall stand according to an embodiment of the present invention can operate in association with a stretcher table, reduce footprint when used independently, and increase movable range of the detector in a vertical direction.

Figure 1A:
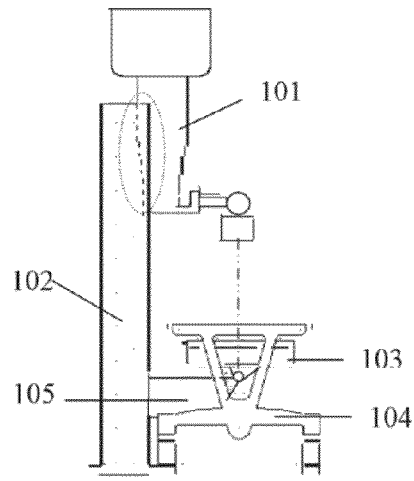
FIG. 1A is a schematic diagram of one kind of prior art wall stand.
Figure 1B:
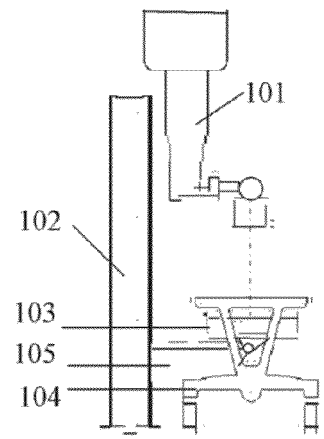
FIG. 1B is a schematic diagram of another kind of prior art wall stand.
Figure 2:
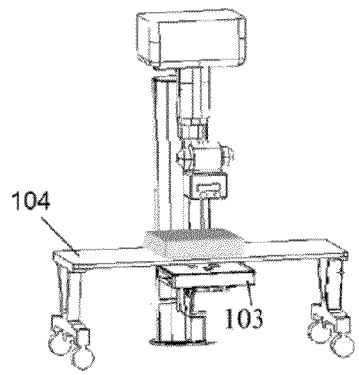
FIG. 2 is a schematic diagram showing operations of chest radiograph mosaicking in the prior art.
Figure 3A:
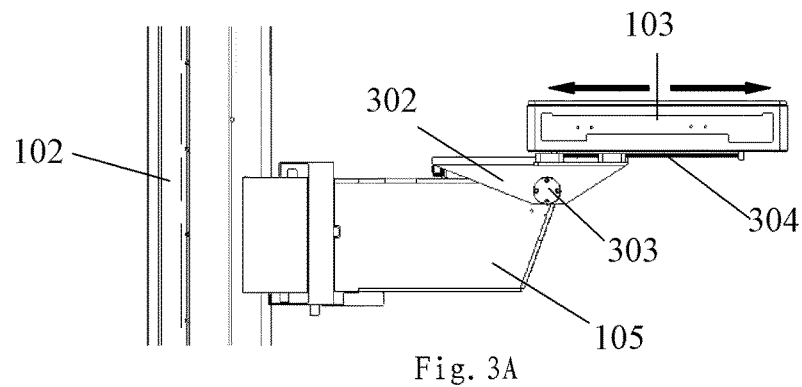
FIGS. 3A and 3B are schematic diagrams of a wall stand according to an embodiment of the present invention.
Figure 3B:
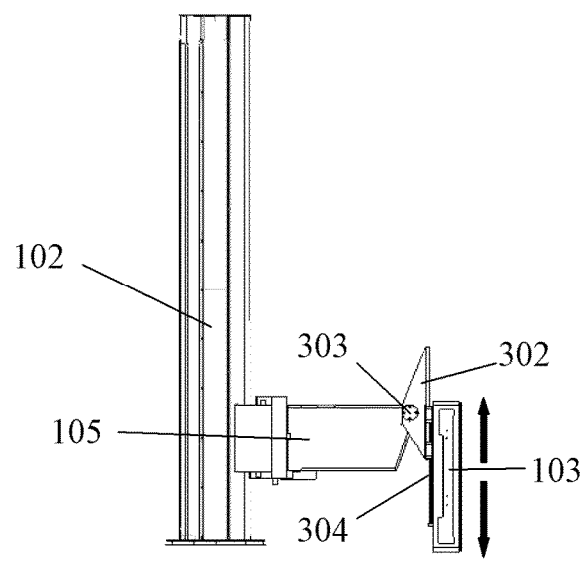

FIGS. 3A and 3B illustrate structure of a wall stand according to an embodiment of the present invention. Said wall stand comprises a column 102, a support arm 105 connected in a direction perpendicular to a height direction of the column 102, a rotary shaft 303 mounted on the support arm 105, a rotary bracket 302 capable of rotating around the rotary shaft 303, a detector box 103 mounted on the rotary bracket 302, and a drive mechanism 304 for the detector box provided between the rotary bracket 302 and the detector box 103. As is also shown in FIG. 3A, the detector box 103 is movable in a plane supported by the rotary bracket 302 in a direction perpendicular to the height direction of the column 102, driven by the drive mechanism 304 for the detector box. FIG. 3B also shows that the detector box 103 is movable in a plane supported by the rotary bracket 302 in a direction parallel to the height direction of the column 102, driven by the drive mechanism 304 for the detector box. Besides, the detector box 103 may also, after being angled to the column 102 to a certain degree with the rotation of the rotary shaft 303, travel in a plane supported by the rotary bracket 302 in a direction perpendicular to an axial direction of the rotary shaft 303, driven by the drive mechanism 304 for the detector box.

Figure 4A:
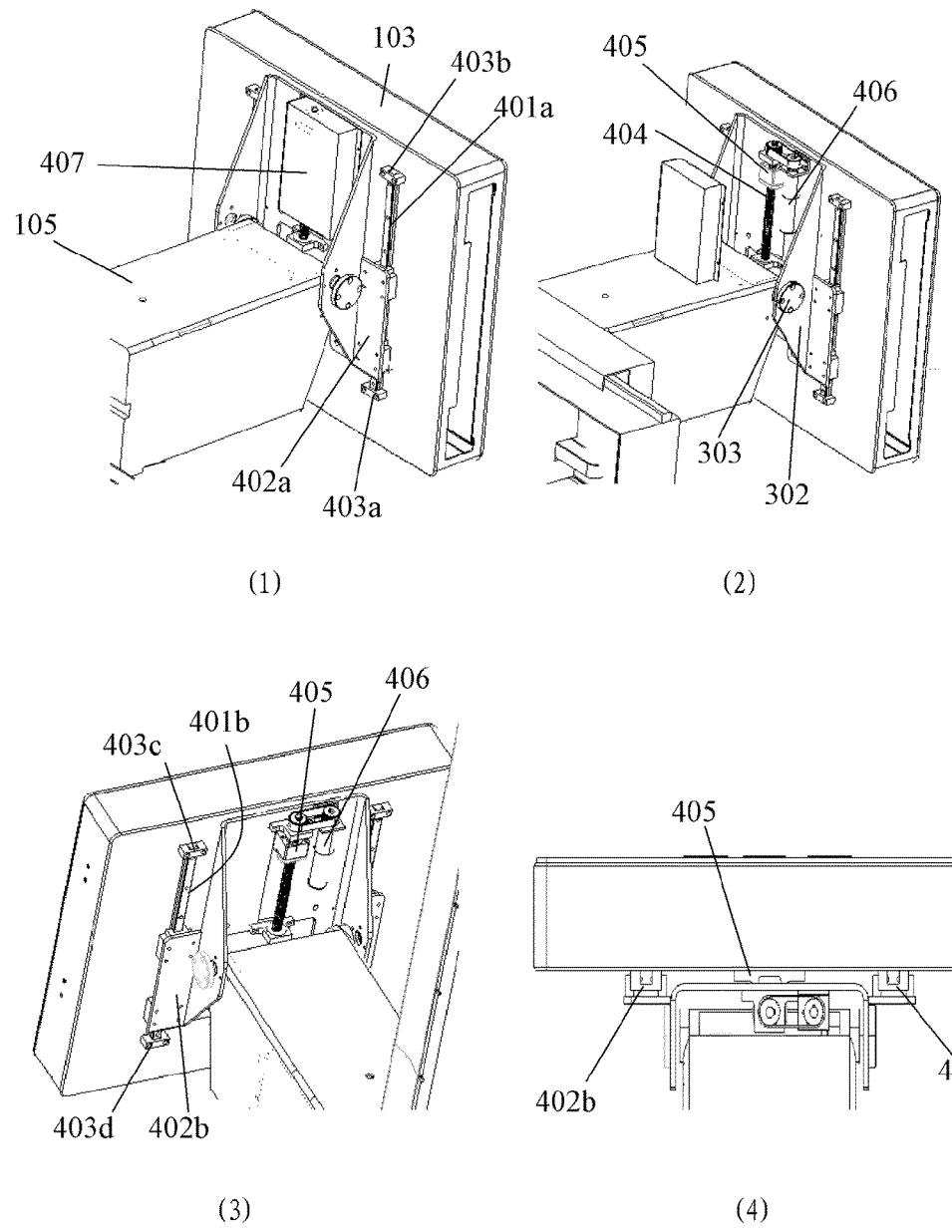
FIGS. 4A (1), (2), (3), (4) are schematic diagrams of a drive mechanism for the detector box of the wall stand according to an embodiment of the present invention.

FIGS. 4A (1), (2), (3) and (4) show a structure of the drive mechanism 304 for the detector box of the wall stand according to an embodiment of the present invention. The drive mechanism comprises at least two guide rails 401a, 401b fixed in parallel to the bottom surface of the detector box 103, at least two sliders 402a, 402b provided on the rotary bracket 302, the slider 402a slidably connected to the guide rail 401a and interlocked with each other, and the slider 402b slidably connected to the guide rail 401b and interlocked with each other, and a power supply 407 for driving the sliders 402a and 402b to reciprocate on the guide rails 401a, 401b respectively, wherein the guide rail 401a is provided with stoppers 403a, 403b at two ends, and the guide rail 401b is provided with stoppers 403c, 403d at two ends.

FIGS. 4A (2), (3) and (4) further illustrate a structure of the power supply 407 from different angles. Said power supply further includes an electric motor 406 fixed on the rotary bracket 302, a leading screw 404 fixed on the rotary bracket 302 and rotatable with the drive of the electric motor 406, and a nut 405 fixed on the bottom surface of the detector box and fitted around the leading screw. After the electric motor 406 is activated, the rotary bracket 302 remains stationary, and the electric motor 406 rotates the leading screw 404, such that the nut 405 moves in an axial direction of the leading screw 404; since the nut 405 is fixedly connected to the detector box 103, then the detector box 103 will also move in the axial direction of the leading screw 404. In actual application, the axial direction of the leading screw 404 is arranged to be perpendicular to the axial direction of the rotary shaft 303, thus ensuring that the detector box 103 moves in a direction perpendicular to the axial direction of the rotary shaft 303.

Figure 4B:
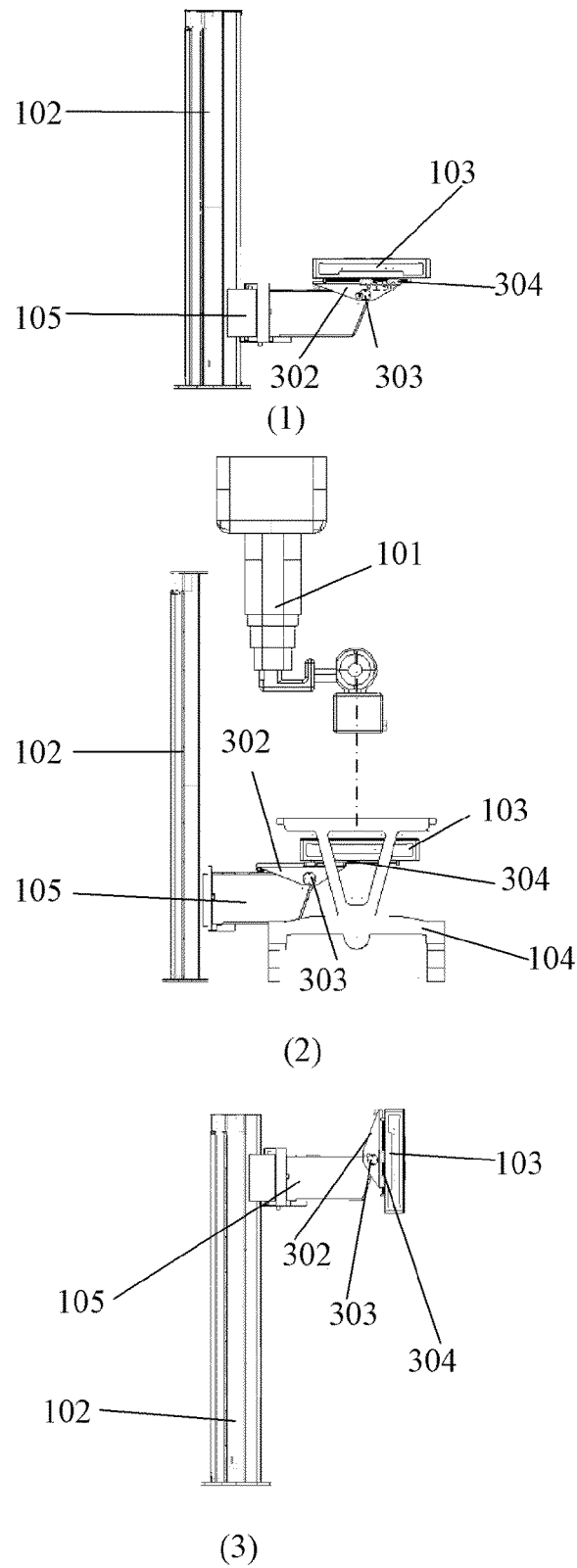
FIGS. 4B (1), (2), (3) are schematic diagrams illustrating operating state of the wall stand according to an embodiment of the present invention.

FIG. 4B shows the operating state of the wall stand according to an embodiment.

FIG. 4B (1) shows a state where the wall stand is used alone. Since the drive mechanism 304 is capable of moving the detector box 103 in a plane supported by the rotary bracket 302 in a direction perpendicular to the axial direction of the rotary shaft 303, the support arm 105 can be designed to be relatively short, when the wall stand is used independently.

FIG. 4B (2) shows a state where the wall stand is used in association with the stretcher table 104. When the wall stand is used in association with the stretcher table 104, the drive mechanism 304 drives the detector box 103 to a position right below the stretcher table 104, thereby ensuring alignment of a central axis of the stretcher table 104 with the overhead tube system 101.

FIG. 4B (3) shows another mode for independent use of the wall stand. When radiographing a standing patient, the rotary bracket 302 and the detector box 103 are first rotated, via the rotary shaft 303, to a position parallel to the height direction of the column 102, and then the support arm 105 is moved in the height direction of the column 102. As is seen in further combination with FIG. 3B, while the height of the column 102 remains unchanged, the movable distance of the detector box 103 in the vertical direction is increased by reason of the drive mechanism 304; or, the column 102 can be designed to be shorter without decreasing the movable distance of the detector box 103 in the vertical direction.

According to an embodiment, the wall stand is further provided with a support arm drive mechanism disposed between the column 102 and the support arm 105, said drive mechanism being for driving said support arm 105, the rotary bracket 302, the rotary shaft 303, and the detector box 103 to move together in a direction perpendicular to the height direction of the column 102.

Figure 5A:
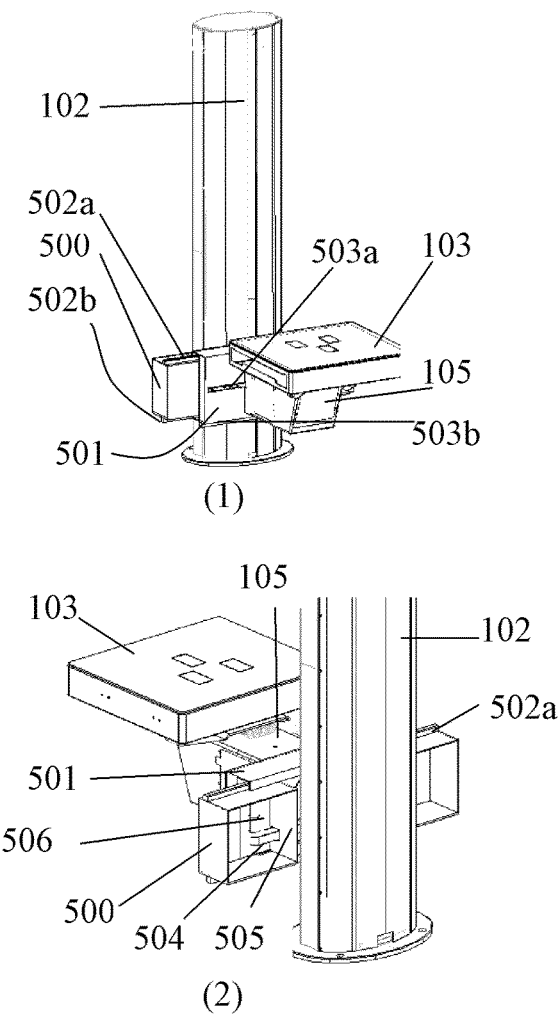
FIGS. 5A (1), (2) are schematic diagrams of a support arm drive mechanism, of the wall stand according to an embodiment of the present invention.

FIGS. 5A (1) and 5A (2) show a structure of the drive mechanism from different perspectives.

As shown in FIG. 5A (1), the drive mechanism includes two driving compartments 500 and 501, two pairs of guide rails 502a, 502b and 503a, 503b, one side of the driving compartment 500 being provided in a direction perpendicular to the height direction of the column 102 and connected to the column and another side opposing to said side being provided with the driving compartment 501. The top and bottom surfaces of the driving compartment 500 are provided with one guide rail 502a, 502b respectively; one side of the driving compartment 501 for connecting to the support arm 105 is provided with one guide rail 503a, and the bottom surface of the driving compartment 501 is provided with one guide rail 503b. The driving compartment 501 is slidably engaged with the guide rails 502a, 502b provided on the top and bottom surfaces of the driving compartment 500, via slip connection members positioned on top and bottom surfaces of the driving compartment 501, such as grooves or sliders. The support arm 105 is slidably engaged with the guide rails 503a, 503b provided on the driving compartment 501, via slip connection members positioned on a side of the support arm for connecting the driving compartment 501 and on a bottom side of the support arm, such as grooves or sliders. Each guide rail is provided with a stopper at both ends.

FIG. 5A (2) shows that the driving compartment 500 further includes an electric motor 506, a leading screw 504 rotatable with the drive of the electric motor, and a nut 505 fixed on the driving compartment 501 and fitted around the leading screw 504. Similarly, the driver compartment 501 also includes an electric motor, a leading screw rotatable with the drive of the electric motor, and a nut fixed on the support arm 105 and fitted around the leading screw.

Of course, one, or two or more driving compartments can be provided according to requirements of actual applications. When more than two driving compartments are provided, similar to the connection structure involving two driving compartments as above, except that the driving compartment in direct slidable connection with the support arm 105 is for driving the support arm, each of the other driving compartments drives a respective slidably connected driving compartment, in a direction starting from the proximity of the column 102 and away from the column 102. Therefore, the movable range of the support arm can be flexibly designed.

Figure 5B:
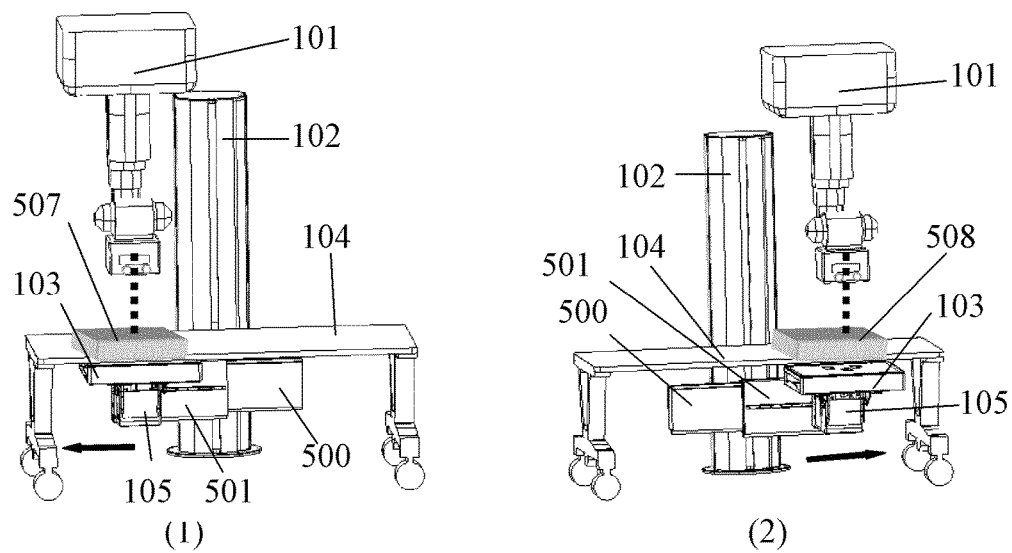
FIGS. 5B (1), (2) are schematic diagrams showing operating state of the wall stand according to an embodiment of the present invention.

FIG. 5B shows an operating state of the wall stand according to an embodiment of the present embodiment.

When the present wall stand is used in association with a stretcher table and the doctor needs to move the patient to take a plurality of chest X-rays for mosaicking, the doctor no longer has to move the stretch table on which the patient lies. The doctor only first needs to take a chest X-ray of an area 507 at a position shown in FIG. 5B (1). Then, while the stretcher table 104 is kept stationary, the support arm 105 and the detector box 103 are driven by the driving compartments 500, 501 to move in a direction perpendicular to the height direction of the column 102, and in the meantime, the overhead tube system 101 moves associatedly in a same direction, such that a different area 508 can be easily radiographed. Further, radiographs of the areas 507, 508 can be mosaicked.

Embodiments of the present invention provide a novel wall stand to address the issues of inability to cooperate a wall stand with a stretcher table or an overlarge footprint of the wall stand that are recognized in prior art wall stands.

An embodiment of the present invention provides a wall stand comprising a column, a detector box, a support arm for the detector box, a rotary shaft mounted on the support arm, a rotary bracket for the detector box capable of rotating around the rotary shaft, wherein said wall stand further comprises a drive mechanism for the detector box capable of moving the detector box in a plane supported by the rotary bracket in a direction perpendicular to an axial direction of the rotary shaft.

An embodiment of the present invention provides a wall stand, wherein the drive mechanism for the detector box comprises at least two parallel guide rails fixed to a bottom surface of the detector box, at least two sliders fixed to the rotary bracket and engaged with the guide rails, and a power supply provided on the rotary bracket.

An embodiment of the present invention provides a wall stand, wherein the power supply further comprises an electric motor, a leading screw rotatable with the drive of the electric motor, and a nut fixed to the bottom surface of the detector box and fitted around the leading screw.

An embodiment of the present invention provides a wall stand, wherein each guide rail is provided with a stopper at both ends.

An embodiment of the present invention provides a wall stand, wherein the wall stand further comprises a support arm drive mechanism provided between the column and the support arm, said support arm drive mechanism being for driving the support arm, the rotary bracket, the rotary shaft, and the detector box to move together in a direction perpendicular to a height direction of the column.

An embodiment of the present invention provides a wall stand, wherein the support arm drive mechanism comprises one driving compartment, one side of the driving compartment being connected to the column in a direction perpendicular to the height direction of the column, and one opposed side thereof being slidably connected to the support arm via a slip connection member.

An embodiment of the present invention provides a wall stand, wherein the support arm drive mechanism comprises a plurality of driving compartments, one side of a first driving compartment being connected to the column in a direction perpendicular to the height direction of the column and one opposed side thereof being provided with a second driving compartment, said second and first driving compartments being connected via a slip connection member, and wherein one side of a farthest driving compartment away from the column is slidably connected to another adjacent driving compartment, and one opposed side thereof is slidably connected to the support arm via a slip connection member.

An embodiment of the present invention provides a wall stand, wherein the slip connection member comprises at least two guide rails, and a slider slidable along the guide rails or a groove matching the guide rails.

An embodiment of the present invention provides a wall stand, wherein the driving compartment further comprises an electric motor, a leading screw rotatable with the drive of the electric motor, and a nut fixed to a driven object and fitted around the leading screw.

An embodiment of the present invention provides a wall stand, wherein each guide rail is provided with a stopper at both ends.

Compared with the prior art, the wall stand according to embodiments of the present invention achieves the following technical effects.

(1) The scope of medical applications of wall stand is extended, such that the wall stand can operate with a stretcher table and meanwhile has a small footprint when used alone.

(2) When the wall stand does not need to operate in association with the stretcher table, the support arm is at least 200 mm shorter than that of those existing wall stands, thereby saving installation space for the wall stand.

(3) When the detector needs to move up and down in the column height direction of the wall stand, the range of movement can be increased by 200 mm, or, for the same range of movement of the detector, the column height can be reduced by 200 mm, which is conducive to the transportation and installation of the product.

(4) When the wall stand is used in association with a stretcher table, it ensures that the detector can be moved to a position at a central axis of the stretcher table, thereby preventing the wall stand from colliding with the overhead tube system.

(5) The wall stand facilitates doctors in taking a plurality of radiographs for mosaicking without necessitating extra strenuous operation, and at the same time, the wall stand improves patient comfort.

What is claimed is:

1. A wall stand, comprising:
   a column;
   a detector box;
   a support arm configured to support the detector box;
   a rotary shaft mounted on the support arm;
   a rotary bracket rotatable around the rotary shaft;
   a drive mechanism configured to move the detector box in a plane supported by the rotary bracket in a direction perpendicular to an axial direction of the rotary shaft; and
   a support arm drive mechanism between the column and the support arm configured to drive the support arm, the rotary bracket, the rotary shaft, and the detector box to move together in a direction perpendicular to a height direction of the column, the support arm driving mechanism comprising a driving compartment comprising a first side connected to the column in a direction perpendicular to the height direction of the column and a second side slidably connected to the support arm through a slip connection member.

2. The wall stand according to claim 1, wherein the slip connection member comprises:
   at least two guide rails; and
   a slider slidable along the at least two guide rails or a groove matching the at least two guide rails.

3. The wall stand according to claim 2, wherein each of the at least two guide rails comprises a stopper at both of their respective outboard ends.

4. The wall stand according to claim 1, wherein the driving compartment comprises:
   an electric motor;
   a leading screw rotatable with a drive of the electric motor; and
   a nut fixed to a driven object and fitted around the leading screw.

5. The wall stand according to claim 1, wherein the drive mechanism comprises:
   at least two parallel guide rails fixed to a bottom surface of the detector box;
   at least two sliders fixed to the rotary bracket and engaged with the guide rails; and
   a power supply on the rotary bracket.

6. The wall stand according to claim 5, wherein the power supply comprises:
   an electric motor;
   a leading screw rotatable with a drive of the electric motor; and
   a nut fixed to the bottom surface of the detector box and fitted around the leading screw.

7. The wall stand according to claim 5, wherein each of the at least two parallel guide rails comprises a stopper at both of their respective outboard ends.

8. A wall stand, comprising:
   a column;
   a detector box;
   a support arm configured to support the detector box;
   a rotary shaft mounted on the support arm;
   a rotary bracket rotatable around the rotary shaft;
   a drive mechanism configured to move the detector box in a plane supported by the rotary bracket in a direction perpendicular to an axial direction of the rotary shaft; and
   a support arm drive mechanism between the column and the support arm configured to drive the support arm, the rotary bracket, the rotary shaft, and the detector box to move together in a direction perpendicular to a height direction of the column, the support arm driving mechanism comprising at least a first driving compartment, a second driving compartment and a third driving compartment, the first driving compartment comprising a first side connected to the column in a direction perpendicular to the height direction of the column and a second connected to the second driving compartment, wherein the second driving compartment and the first driving compartment are connected through a first slip connection member, and wherein a first side of the third driving compartment is slidably connected to another adjacent driving compartment and a second side of the third driving compartment is slidably connected to the support arm through a second slip connection member.

9. The wall stand according to claim 8, wherein at least one of the first slip connection member and the second slip connection member comprises:
   at least two guide rails; and
   a slider slidable along the at least two guide rails or a groove matching the at least two guide rails.

10. The wall stand according to claim 9, wherein each of the at least two guide rails comprises a stopper at both of their respective outboard ends.

11. The wall stand according to claim 8, wherein at least one of the plurality of driving compartments comprises:
   an electric motor;
   a leading screw rotatable with a drive of the electric motor; and
   a nut fixed to a driven object and fitted around the leading screw.

12. A wall stand, comprising:
   a column;
   a detector box;
   a support arm configured to support the detector box;
   a rotary shaft mounted on the support arm;
   a rotary bracket rotatable around the rotary shaft;
   a drive mechanism configured to move the detector box in a plane supported by the rotary bracket; and
   a support arm drive mechanism between the column and the support arm configured to drive the support arm, the rotary bracket, the rotary shaft, and the detector box to move together, the support arm driving mechanism comprising a driving compartment slidably connected to the support arm through a slip connection member.

13. The wall stand according to claim 12, wherein the drive mechanism is configured to move the detector box in a plane supported by the rotary bracket in a direction perpendicular to an axial direction of the rotary shaft.

14. The wall stand according to claim 12, wherein the support arm is configured to drive the support arm, the rotary bracket, the rotary shaft, and the detector box to move together in a direction perpendicular to a height direction of the column.

15. The wall stand according to claim 12, wherein the first side of the driving compartment is connected to the column in a direction perpendicular to the height direction of the column.

* * * * *